United States Patent
Hoeg et al.

(10) Patent No.: US 7,344,494 B2
(45) Date of Patent: Mar. 18, 2008

(54) ENDOSCOPE WITH VARIABLE DIRECTION OF VIEW MODULE

(75) Inventors: Hans David Hoeg, Arcadia, CA (US); Eric Lawrence Hale, Altadena, CA (US); Nathan Jon Schara, Pasadena, CA (US)

(73) Assignee: Karl Storz Development Corp., Goleta, CA (US)

( * ) Notice: Subject to any disclaimer, the term of this patent is extended or adjusted under 35 U.S.C. 154(b) by 312 days.

(21) Appl. No.: 11/048,021

(22) Filed: Jan. 31, 2005

(65) Prior Publication Data

US 2005/0177026 A1     Aug. 11, 2005

Related U.S. Application Data

(60) Provisional application No. 60/542,943, filed on Feb. 9, 2004.

(51) Int. Cl.
*A61B 1/06* (2006.01)
(52) U.S. Cl. .................. 600/173; 600/170; 600/171
(58) Field of Classification Search ............. 600/103, 600/129, 137, 170–175
See application file for complete search history.

(56) References Cited

U.S. PATENT DOCUMENTS

| | | | |
|---|---|---|---|
| 3,856,000 A | 12/1974 | Chikama | 128/6 |
| 3,880,148 A | 4/1975 | Kanehira et al. | 128/6 |
| 4,037,938 A | 7/1977 | Yamashita et al. | 350/202 |
| 4,042,295 A | 8/1977 | Yamasita et al. | 350/202 |
| 4,140,364 A | 2/1979 | Yamashita et al. | 350/26 |
| 4,598,980 A | 7/1986 | Doi et al. | 350/445 |
| 4,697,577 A | 10/1987 | Forkner | 128/6 |
| 5,313,306 A | 5/1994 | Kuban et al. | 348/65 |
| 5,524,180 A | 6/1996 | Wang et al. | 600/118 |
| 5,762,603 A | 6/1998 | Thompson | 600/112 |
| 5,800,341 A | 9/1998 | McKenna et al. | 600/109 |
| 6,097,423 A | 8/2000 | Mattsson-Boze et al. | 348/65 |
| 6,190,309 B1 * | 2/2001 | Ooshima et al. | 600/179 |
| 6,371,909 B1 | 4/2002 | Hoeg et al. | 600/173 |
| 6,500,115 B2 | 12/2002 | Krattiger | 600/173 |
| 6,560,013 B1 | 5/2003 | Ramsbottom | 359/431 |
| 6,648,817 B2 | 11/2003 | Schara et al. | 600/173 |
| 6,663,559 B2 | 12/2003 | Hale et al. | 600/118 |
| 6,958,034 B2 * | 10/2005 | Iddan | 600/114 |
| 2001/0031912 A1 | 10/2001 | Adler | 600/109 |
| 2001/0035902 A1 | 11/2001 | Iddan et al. | 348/76 |
| 2002/0068853 A1 | 6/2002 | Adler | 600/160 |
| 2004/0249247 A1 * | 12/2004 | Iddan | 600/170 |
| 2005/0085698 A1 * | 4/2005 | Bonningue | 600/170 |

FOREIGN PATENT DOCUMENTS

| | | |
|---|---|---|
| DE | 299 07 430 | 9/1999 |
| WO | WO 99/42028 | 8/1999 |
| WO | WO 01/22865 | 4/2001 |

* cited by examiner

*Primary Examiner*—John P. Leubecker
*Assistant Examiner*—Philip R Smith
(74) *Attorney, Agent, or Firm*—St. Onge Steward Johnston & Reens LLC (57) ABSTRACT

A flexible variable direction of view endoscope with a pivotable view vector and a rotatable distal section.

20 Claims, 9 Drawing Sheets

Fig. 1

Prior Art

Prior Art

Fig. 3

Prior Art

ENDOSCOPE WITH VARIABLE DIRECTION OF VIEW MODULE

CROSS-REFERENCE TO RELATED APPLICATIONS

This application claims the benefit of U.S. provisional application Ser. No. 60/542,943 filed on Feb. 9, 2004, entitled "Endoscope with variable direction of view module," the contents of which are incorporated herein by reference.

FIELD OF THE INVENTION

The present invention relates to variable direction of view endoscopes and applies primarily to flexible endoscopes.

BACKGROUND OF THE INVENTION

The purpose of variable direction of view endoscopes is to provide greater viewing mobility. Variable direction of view endoscopes come in two general classes: rigid and flexible. Rigid variable direction of view scopes either change their line of sight mechanically, as disclosed in U.S. Pat. No. 3,856,000 to Chikama, U.S. Pat. No. 6,371,909 to Hoeg, U.S. Pat. No. 6,560,013 to Ramsbottom, U.S. Pat. No. 4,697,577 to Forkner, U.S. Pat. No. 6,500,115 to Krattiger et al., and U.S. Pat. No. 5,762,603 to Thompson, or electronically, as disclosed in U.S. Pat. No. 5,313,306 to Kuban, and U.S. Pat. No. 5,800,341 to McKenna et al. The first advantage with these designs is that they allow wide range scanning without having to move the endoscope, making them ideal for inspecting small cavities. The view vector can be rotated about the longitudinal axis of the scope (pan), and about an axis normal to the endoscope shaft (tilt) to cover a large solid angle. Typically, these two degrees of freedom are rigidly actuated from the proximal end of the endoscope. Because these scopes rigidly transmit motion from the operator to the view vector, the view is relatively easy to control, a key advantage.

These rigid mechanisms also have the advantage of being kinematically determinate, which means that there is a known mathematical relationship between the distal and proximal ends. That is, based on the structure of the endoscope there is an available linear transformation (in robotics called the Forward Kinematic Transformation) which can be used to compute the endoscopic viewing configuration based on input from proximal accelerometers and encoders. This transformation makes it possible to implement electronic control, as disclosed in U.S. Pat. No. 6,663,559 to Hale et al. who teach the use of computer-controlled actuators and sensors to position the view vector and thus provide the endoscope with advanced navigation capabilities. Along related lines U.S. Pat. No. 5,524,180 to Wang et al. teaches a robotic positioning system for endoscopes, and U.S. Pat. No. 6,097,423 to Chatenever et al proposes the use of sensors and actuators to control the endoscopic image orientation. The successful operation of all these systems relies on having a known mathematical relationship between the distal and proximal ends of the instrument.

Unlike rigid scopes, flexible variable direction of view endoscopes change their viewing direction by deflecting the entire distal section of the instrument. Their main advantage over rigid scopes is that they can reach certain areas not accessible by rigid instruments. Otherwise they are inferior in the following ways:

Restricted mobility. Because they must flex in order to change their line of sight, mobility is restricted in small cavities. Specifically, the tip can not actuate properly if it is too close to a wall.

Unknown viewpoint. It is often difficult for the user to stay oriented when using flexible endoscopes because the view point displaces itself in a confusing way as the tip is flexed. Kanehira (U.S. Pat. No. 3,880,148) tried to solve these problems by incorporating a pivotable distal reflector as seen in rigid variable direction of view scopes, but the design was too complex, and it suffered from another fundamental shortcoming of flexible endoscopes: shaft wind-up.

Shaft wind-up. A flexible shaft cannot predictably transmit twisting motions. Unlike rigid variable direction of view endoscopes which can rely on rigid transmission of a torsional moment through their shaft to obtain the necessary second degree of view vector freedom at the tip, flexible endoscopes tend to wind up and do not reliably transmit twisting motions from the proximal to the distal end. This is because the surrounding tissue exerts sufficient frictional force to counteract twist force from the operator. This problem is so severe that makers of flexible endoscopes eventually designed four-way tip deflection mechanisms in an attempt to regain some of the mobility lost through shaft wind-up. Stored torsional energy can also cause a wound scope to release unexpectedly, possibly injuring tissue.

Indeterminate kinematics. Besides reduced controllability from twisting and bending, the flexible nature of the endoscope shaft introduces a further complication: the kinematic relationship between the distal and proximal ends is unknown. Because a flexible shaft accommodates the geometry/topography of its surroundings, the configuration of the endoscope tip and its view vector can not be correctly computed from sensor inputs at the proximal end. This means that unless the tip or shaft is instrumented with sensors, it is impossible to provide advanced navigation features (such as those described by Hale et al.).

Decoupled viewing process. Another drawback resulting from the mathematical decoupling between the distal and proximal ends is that the scope's viewing direction can not be mentally visualized by the operator during use. Getting an external estimate of where an endoscope is "looking" during a procedure is important as the clinician tries to integrate preexisting knowledge of the anatomy with the viewing process. With rigid fixed-viewing endoscopes the operator can extrapolate the viewing direction as an extension of the longitudinal axis of the endoscope even though the tip is concealed by surrounding tissue. With rigid variable viewing direction instruments the configuration of the view vector is kinematically determinate and so can be presented graphically to the user (Hale et al). Neither of these advantages is possible with current flexible endoscopes.

The results of these shortcomings are poor controllability, operator disorientation, inconsistent diagnoses from one operator to the next, disjunct viewing coverage, reduced ability to produce diagnostic maps, and difficulty returning to a previous view for biopsy.

Accordingly, the primary object of the present invention is to provide a flexible endoscope with the capabilities and advantages of a rigid variable direction of view endoscope. Another object of the present invention is to make flexible endoscopes more compatible with computer-aided naviga-

BRIEF SUMMARY OF THE INVENTION

In accordance with the present invention, a flexible endoscope has a pivotable view vector, a distal section rotatable about its longitudinal axis, a distal image sensor, distal actuators, distal sensors, and a solid state illumination system.

DETAILED DESCRIPTION OF THE INVENTION

The following detailed description illustrates the invention by way of example, not by way of limitation of the principles of the invention. This description will enable one skilled in the art to make and use the invention, and describes several embodiments, adaptations, variations, alternatives and uses of the invention, including what we presently believe is the best mode of carrying out the invention.

Prior Art Devices

Figure 1:
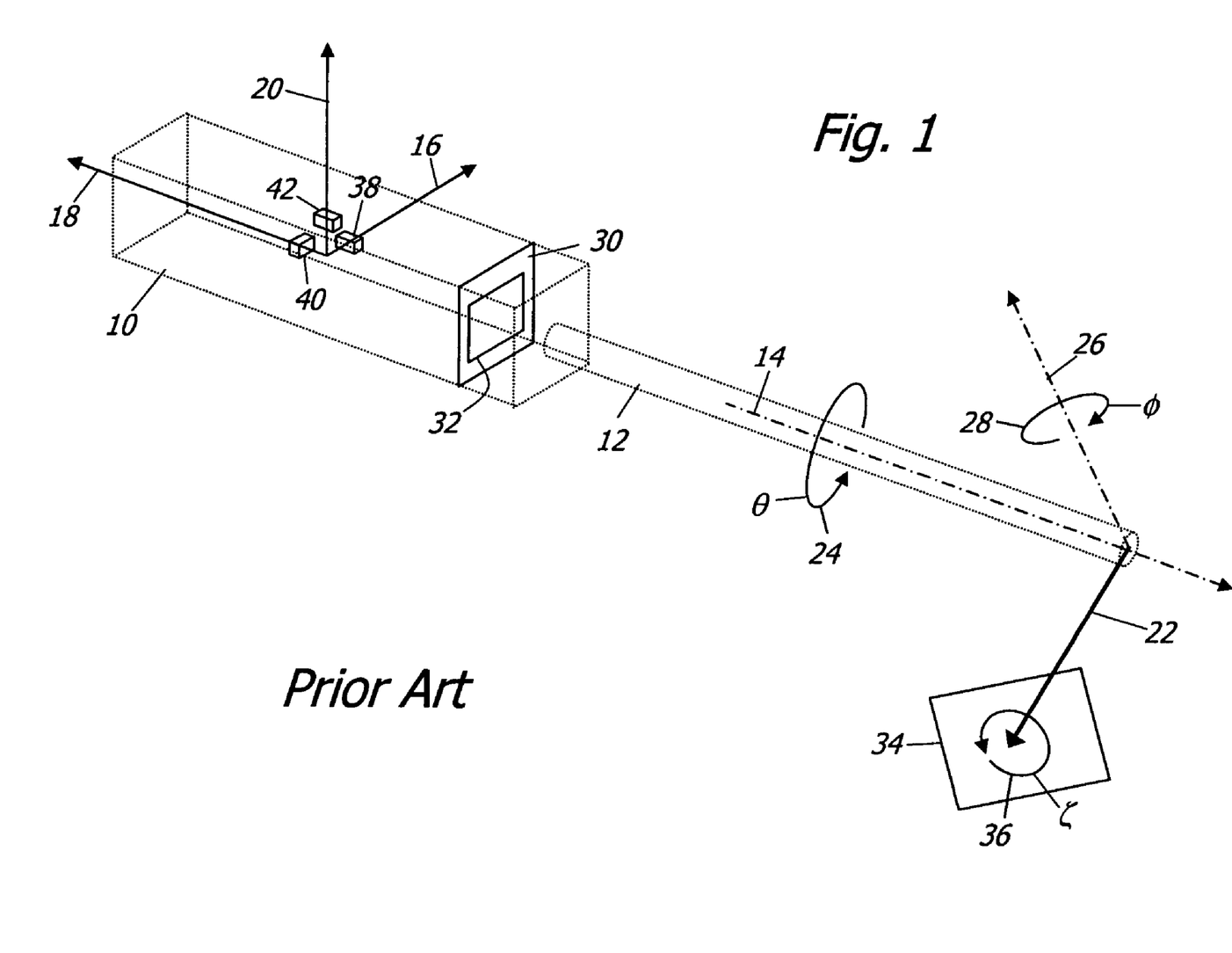
FIG. 1 shows the operating principle of a rigid variable direction of view endoscope and an example of a parameterization of the view vector coordinates relative to the coordinates of the endoscope frame.

Referring now to the drawings, in which like reference numbers represent similar or identical structures throughout, FIG. 1 shows a parameterization of a rigid variable direction of view endoscope consisting of a handle 10 and a shaft 12 with a longitudinal axis 14. The handle 10 can be parameterized by coordinate axes 16, 18, 20 which provide a reference frame for describing the relative motion of a variable view vector 22. The view vector 22 can be rotated about the longitudinal axis 14 in a first degree of freedom 24 and about a second axis 26 in a second degree of freedom 28. A camera 30 (which could also be located in the endoscope tip) produces an image 32 of the endoscopic view 34. Rotation of the image 32 constitutes a third degree of freedom 36. Encoders and processors (not shown) monitor the states of the three degrees of freedom 24, 28, 36 and provide information about the running configuration of the endoscope relative to its default configuration. The default configuration is the basic reference state of the endoscope and is important in calculating viewing configurations corresponding to desired views requested by the operator. Some variable direction of view endoscopes will also include accelerometers 38, 40, 42 which measure roll, pitch and yaw of the endoscope handle 10 and thus provide the information necessary to enable gravity referenced navigation of the view 34. Whether the viewing navigation is gravity referenced, view referenced, or scope frame referenced, it fundamentally relies on the rigid and thus measurable relationship between the distal mechanics of the endoscope and its proximal handle 10.

Figures 2A, 2B:
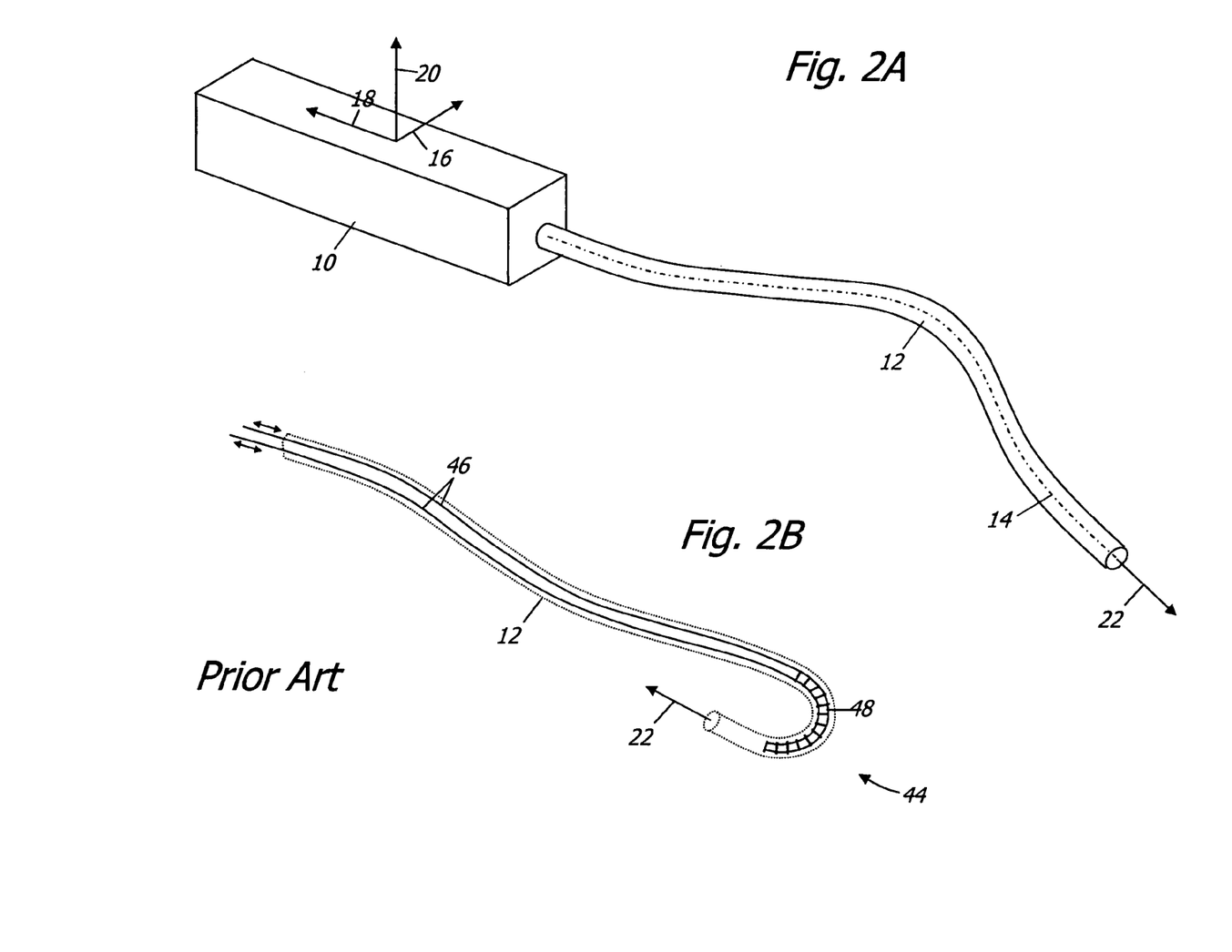
FIG. 2A shows how the distal view vector coordinates of a flexible endoscope are arbitrary/unknown relative to the proximal coordinates of frame/handle.
FIG. 2B shows the concept of a flexible endoscope shaft which can be deflected at the tip by internal cables.

FIGS. 2A and 2B respectively show a flexible endoscope and a flexible endoscope shaft 12 with a deflectable tip 44 actuated by cables 46 connected to distal vertebra 48. Because the longitudinal axis 14 is variable and curvilinear, the direction of view vector 22 relative to the handle 10 and coordinate axes 16, 18, 20 is unknown. There is also no default configuration for the endoscope from which to compute viewing motion. Gravity referenced navigation also becomes impossible with proximally placed accelerometers because the attitude of the handle 10 is not correlated to the attitude of the endoscope tip.

Figure 3:
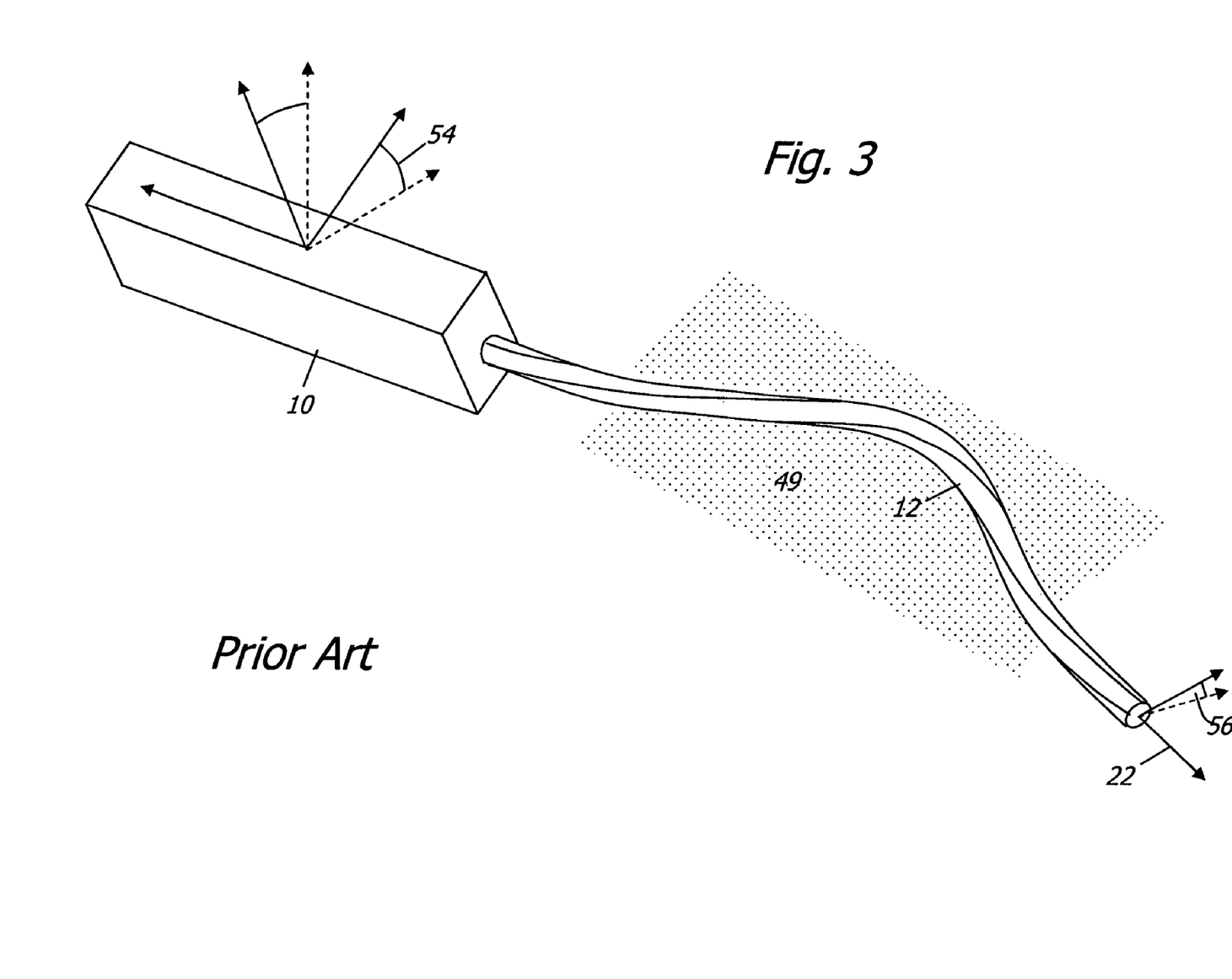
FIG. 3 illustrates the concept of torsional wind-up of a flexible endoscope.

FIG. 3 illustrates torsional wind-up of a flexible endoscope shaft 12 caused by frictional forces from the surroundings 49. As the endoscope handle 10 is twisted from an initial configuration to a new configuration through an angle 54, the proximal end of the endoscope shaft 12 follows the motion of the handle 10 while the distal end only twists through a smaller angle 56. This wind-up is responsible for complete or partial loss of the first degree of freedom.

Preferred Embodiment

Figure 4A:
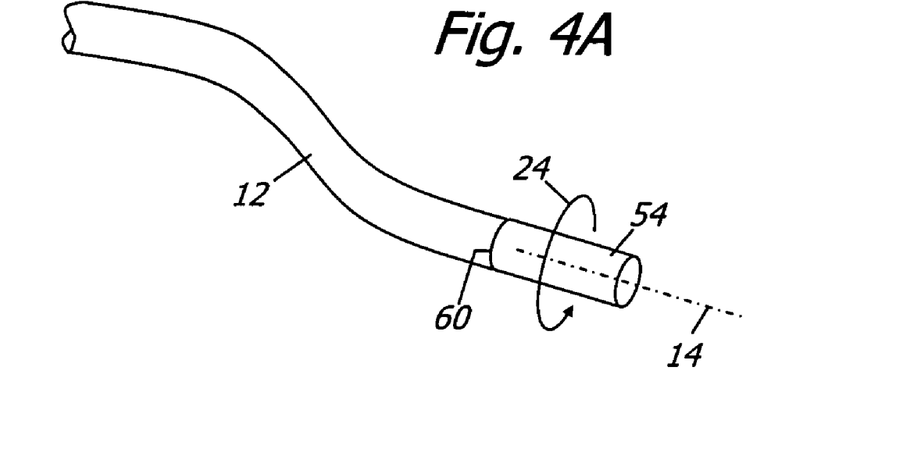
FIGS. 4A, 4B, and 4C schematically show the principle of an independently rotatable distal section of a flexible endoscope and various ways of actuating this distal section.
Figure 4B:
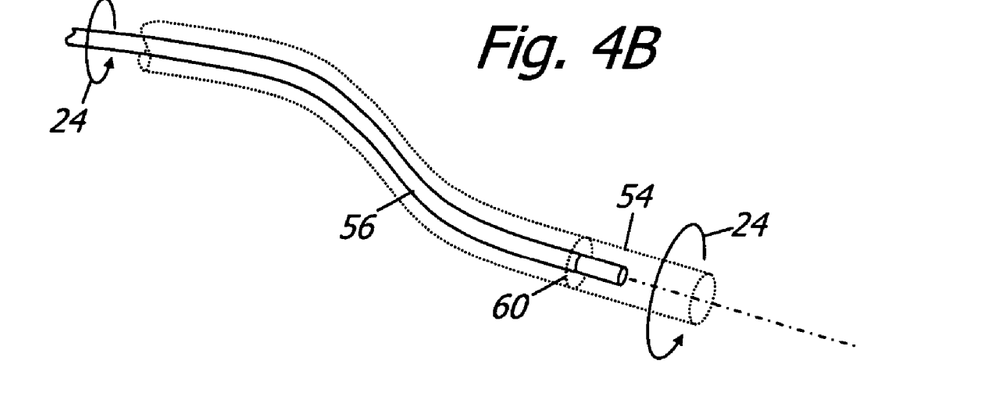

Shaft wind-up can be solved by requiring only a section of the shaft to rotate, thus reducing environmental frictional forces. FIG. 4A shows a distal section 54 which is rotatable relative to a stationary shaft 12. The distal section 54 is anchored to a flexible drive shaft 56 similar to speedometer cable, as shown in FIG. 4B. Because the drive shaft 56 is not subjected to frictional forces from the environment, it can be as compliant as the outside shaft 12 and still provide sufficient torque to the distal section 54. Alternately an actuator such as a motor 58, can be used to rotate the distal section 54. The motor 58 could be housed in either the shaft 12 or the distal section 54. The interface 60 between the distal section 54 and the shaft 12 can be a rotating seal or it can be covered with a thin sleeve in applications which have strict sterilization requirements. These drive mechanisms do not preclude vertebral or other type of tip deflecting mechanisms positioned in the shaft 12.

Figure 5:
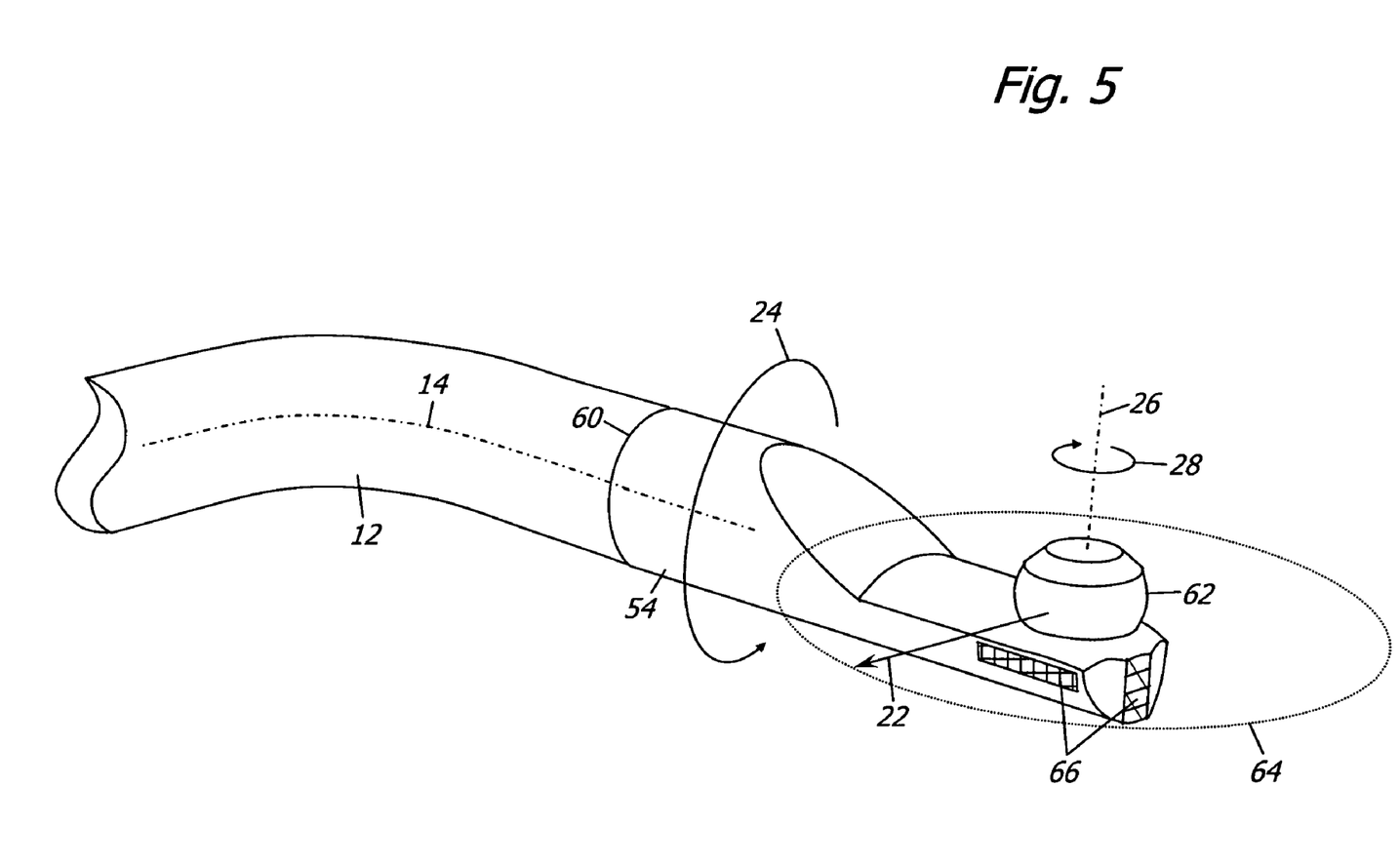
FIG. 5 illustrates a flexible endoscope shaft with a two degree of freedom distal section for variable direction viewing.

The second degree of freedom required for variable direction of view endoscopy is typically provided through optical elements configured to rotate about an axis 26 normal to the endoscope longitudinal axis 14. This is schematically illustrated in FIG. 5, which shows a flexible shaft 12 with a rigid distal section 54 having two degrees of freedom 24, 28. The configuration of the distal section 54, which is similar to that disclosed in U.S. Pat. No. 6,648,817 to Schara et al., has a pivotable view vector 22, a spherical coverglass 62 allowing scanning through a range 64, and a recessed portion behind the coverglass 62 for maximal retroviewing. Illumination is provided by LED arrays 66 which receive power through a rotating electrical connection (not shown) at the interface 60. Illumination could also be provided through traditional optical fibers, but this would require either a fiber optic slip ring, as disclosed in U.S. Pat. No. 5,621,830 to Lucey, or slack fibers which would impose a limited travel on the first degree of freedom 24.

Figure 6A:
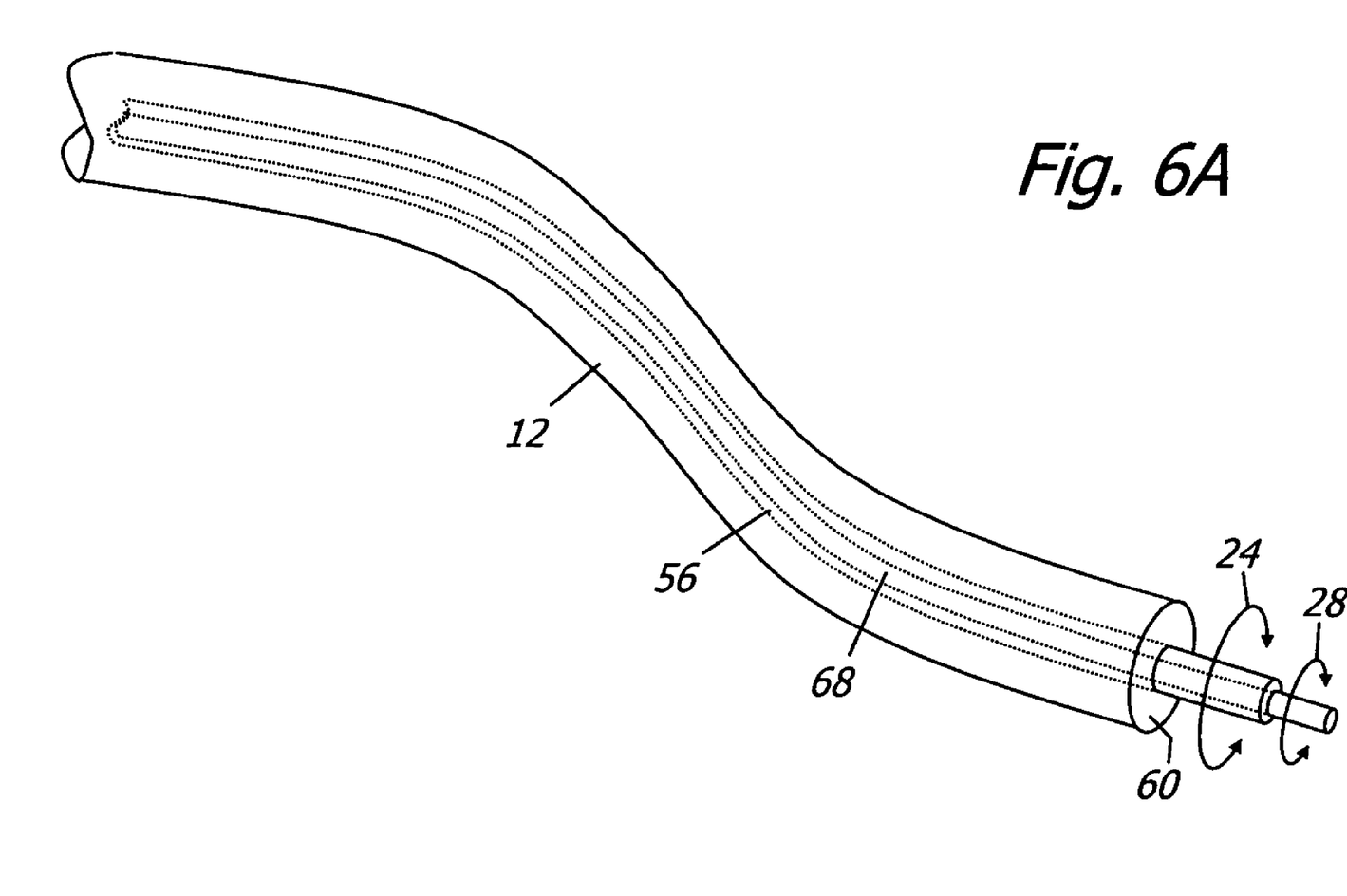
FIG. 6A schematically shows the principle of concentric flexible drive shafts for actuating two degrees of freedom.
Figure 6B:
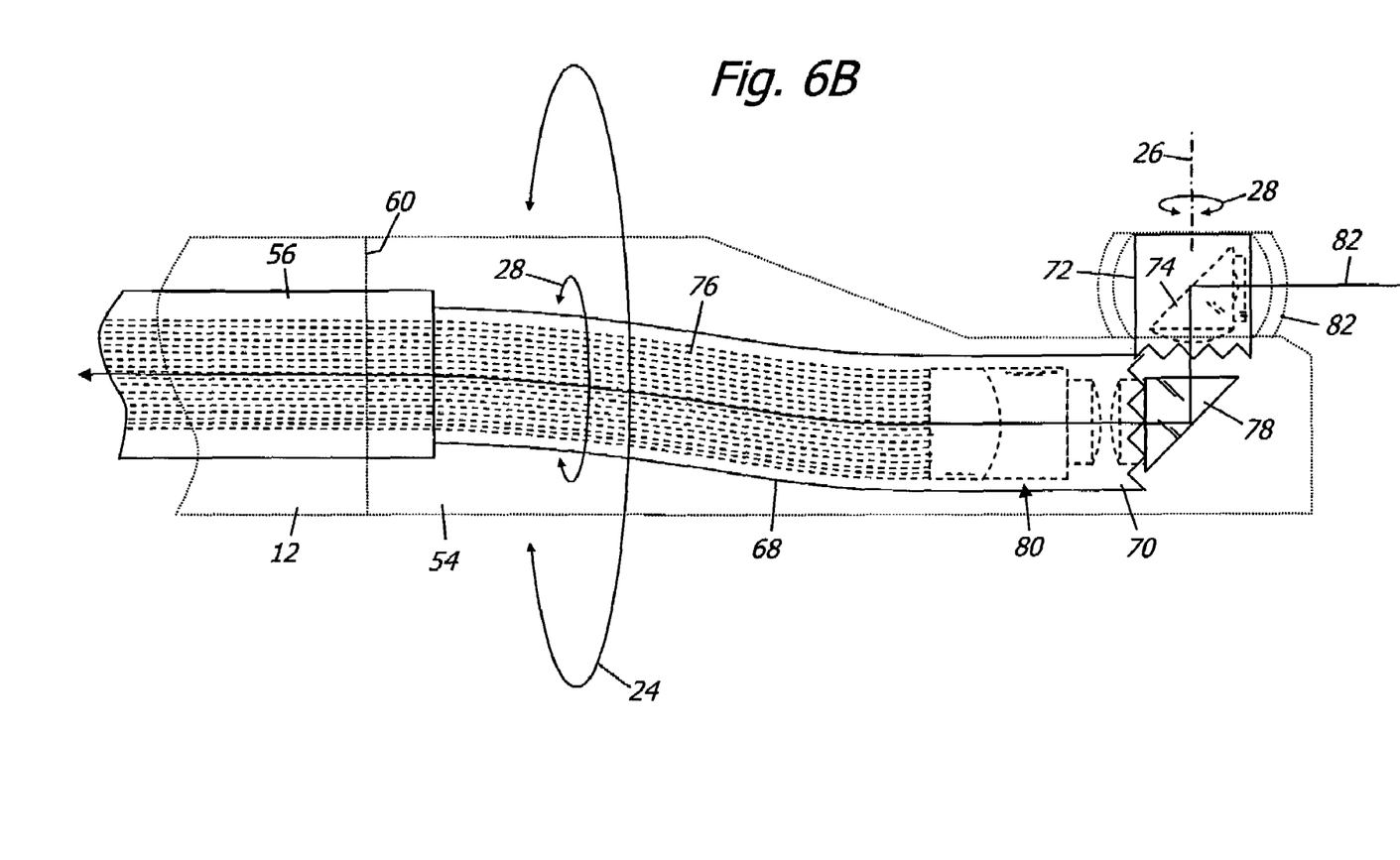
FIG. 6B schematically shows the internal structure of the distal section of a flexible variable direction of view endoscope actuated by concentric flexible drive shafts.

The second degree of freedom 28 can be actuated by another flexible drive shaft 68 routed through the core of the drive shaft 56 which actuates the first degree of freedom 24, as shown in FIG. 6A. This shaft 68 is outfitted with a drive gear 70 and mechanically couples to a driven gear 72, both illustrated in FIG. 6B. The driven gear 72 houses a first reflector 74 and can be rotated about the axis 26. Light from the environment is delivered to a fiber optic relay 76 through the coverglass 62, the first reflector 74, a second reflector 78, and a lens train 80 along a folded optical path 82. In this embodiment the hollow drive shaft 68 houses the fiber relay 76 and thus accomplishes both mechanical and optical transmission. The drive shaft 56 is anchored to the distal section 54 and can be rotated independently of the shaft 68. The drive shafts 56, 68 can be arranged concentrically, but this is not necessary.

Figure 4C:
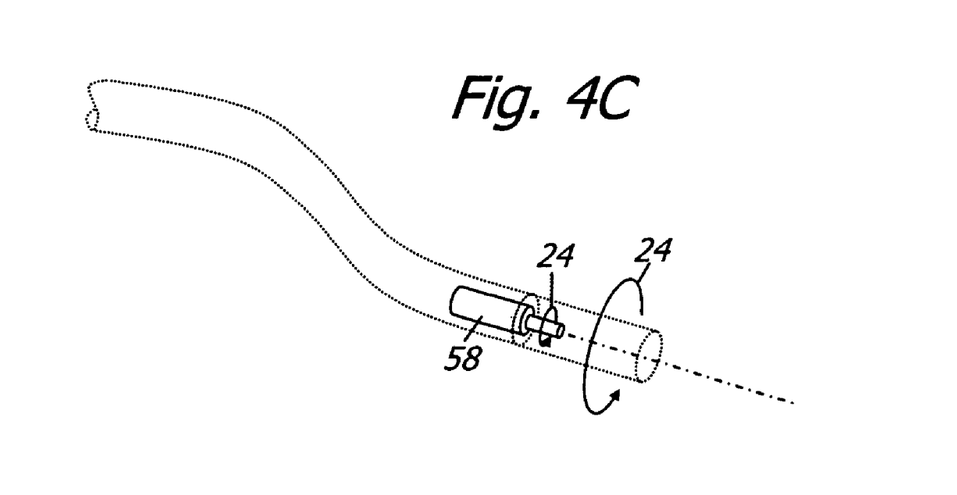
Figure 7A:
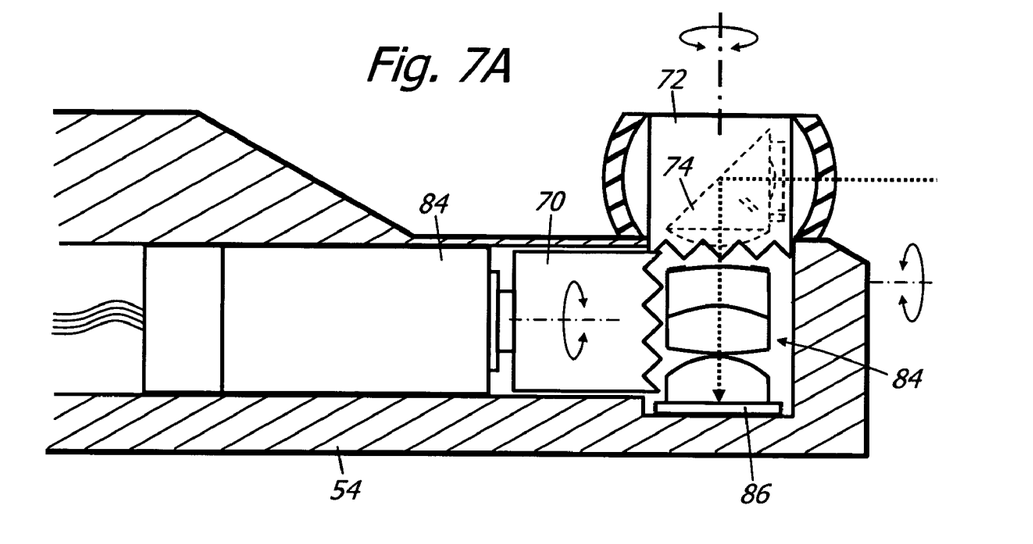
FIGS. 7A and 7B show sectionals of embodiments of distal sections of a variable direction of view endoscope.
Figure 7B:
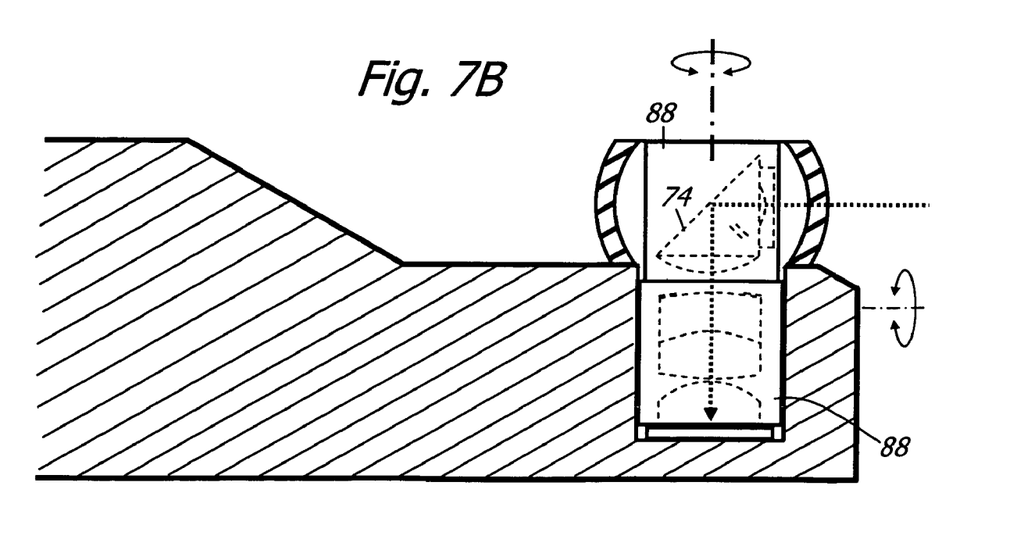

FIG. 7A shows an alternative embodiment of the distal section 54 where the drive shaft for the second degree of freedom has been replaced by a motor 84, and the fiber optic relay has been substituted with a distal image sensor 86, eliminating the need for a second reflector in the lens train 80. In FIG. 7B the reflector 74 is driven directly by a hollow-shaft motor 88 without the use of gears 70, 72. Both of these designs have the advantage of not needing a lengthy optical transmission system or a lengthy mechanical transmission for the second degree of freedom. In either case, the first degree of freedom 24 can be driven by either a flexible shaft or a distal actuator (FIGS. 4B, 4C).

Figure 8:
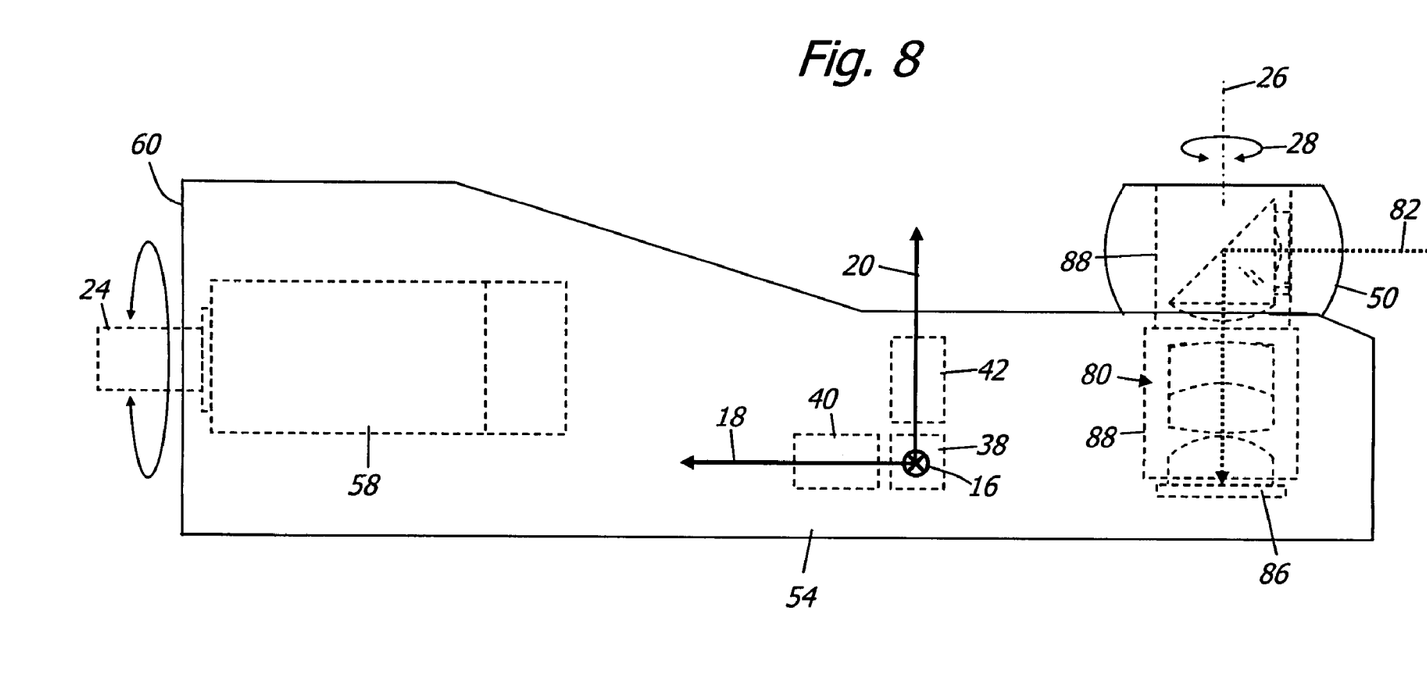
FIG. 8 illustrates a self-contained distal section of a variable direction of view endoscope containing an image sensor, an optical objective system, electromechanical actuators for two degrees of view vector freedom, and accelerometers for sensing pitch, roll, and yaw.

FIG. 8 illustrates distal section 54 as a complete self-contained module which houses actuators 58, 88 for the two degrees of freedom 24, 28, an image sensor 86 with an optical objective system 80, and accelerometers 38, 40, 42 for sensing roll, pitch, and yaw, enabling gravity referenced navigation. These accelerometers could also be placed in the flexible endoscope shaft as long as they are close enough to the tip that there is a fixed geometric relationship between the accelerometers and the tip mechanics. The coordinate axes 16, 18, 20 can be oriented according to a desired parameterization. The module 54 would also be equipped with a solid state illumination system (not shown) and optionally a battery which would remove the need for supplying power through a rotating electrical connection at the interface 60. (An endoscope with a distal module is disclosed in U.S. patent applications 20010031912 and 20020068853 by Adler. These disclosures are however centered on imaging catheters designed to look through blood in veins and arteries and are not concerned with variable direction viewing. Also, U.S. patent application publication 20010035902 teaches a capsule endoscope, but this is a passive system suited solely for imaging the intestinal system, and it is further not concerned with variable direction viewing.)

In a certain embodiment the module 54 could be made detachable from the main endoscope shaft, possibly affording sterilization, storage, manufacturing, and cost advantages. An example of a detachable module is the Karl Storz DCI system which has a detachable shaft and optical relay sterilizable separately from a motorized electromechanical imaging unit. However, this system is not multidirectional and also has the actuators and sensors in the proximal rather than distal end.

Accordingly, the present invention provides a flexible endoscope with the capabilities and advantages of a rigid variable direction of view endoscope. The modularity of this invention could also afford certain advantages to the fields of rigid and semi-flexible variable direction of view endoscopy.

The present invention has been described above in terms of a presently preferred embodiment so that an understanding of the present invention can be conveyed. However, many alternative designs and structural arrangements are possible without departing from the principle of the invention. The scope of the present invention should therefore not be limited by the embodiments illustrated, but rather it should be understood that the present invention has wide applicability with respect to multi-directional viewing instruments. All modifications, variations, or equivalent elements and implementations that are within the scope of the appended claims should therefore be considered within the scope of the invention.

We claim:

1. A variable direction of view endoscope with a modular distal section comprising:

a main shaft, wherein said main shaft is flexible;

a rigid distal section connected to said main shaft and having a longitudinal axis, wherein said rigid distal section is rotatable relative to said main shaft;

a drive member that rotates said distal section about said longitudinal axis and relative to said main shaft;

a reflector disposed in said distal section pivotable about a pivot axis generally transverse to said longitudinal axis;

a drive member that rotates said reflector relative to said distal section; and an objective optical system disposed in said distal section.

2. The apparatus of claim 1, wherein said drive member that rotates said distal section comprises a flexible first internal shaft running down the interior of said main shaft.

3. The apparatus of claim 2, wherein said drive member that rotates said reflector comprises a second internal shaft within said first internal shaft.

4. The apparatus of claim 3, wherein said second internal shaft houses a fiber optic bundle.

5. The apparatus of claim 1, further comprising an image sensor disposed in said distal section.

6. The apparatus of claim 1, wherein said drive member that rotates said distal section comprises an actuator disposed in said main shaft.

7. The apparatus of claim 1, wherein said drive member that rotates said distal section comprises an actuator disposed in said distal section.

8. The apparatus of claim 1, wherein said drive member that rotates said reflector comprises an actuator disposed in said distal section.

9. The apparatus of claim 1, further comprising a rotation pick-up device disposed in said distal section.

10. The apparatus of claim 9, wherein said rotation pick-up device comprises at least one accelerometer.

11. The apparatus of claim 1, further comprising an illumination source disposed in said distal section.

12. A variable direction of view endoscope with a modular distal section, comprising:

a main shaft;

a rigid distal section connected to said main shaft and having a longitudinal axis, wherein said rigid distal section is rotatable relative to said main shaft;

a drive member that rotates said distal section about said longitudinal axis and relative to said main shaft;

a reflector disposed in said distal section pivotable about a pivot axis generally transverse to said longitudinal axis;

a drive member that rotates said reflector relative to said distal section; and an objective optical system disposed in said distal section;

a slip-ring for providing electrical power across the rotary interface between said main shaft and said distal section.

13. The apparatus of claim 12, wherein said drive member that rotates said distal section comprises a flexible first internal shaft running down the interior of said main shaft.

14. The apparatus of claim 12, wherein said drive member that rotates said reflector comprises a second internal shaft within said first internal shaft.

15. The apparatus of claim 12, further comprising an image sensor disposed in said distal section.

16. The apparatus of claim 12, further comprising a rotation pick-up device disposed in said distal section.

17. The apparatus of claim 12, wherein said rotation pick-up device comprises at least one accelerometer.

18. The apparatus of claim 12, further comprising an illumination source disposed in said distal section.

19. A variable direction of view endoscope with a modular distal section comprising:

a main shaft;

a rigid distal section connected to said main shaft having a longitudinal axis, wherein said rigid distal section is rotatable relative to said main shaft;

a means for rotating said distal section relative to said main shaft;

a reflector disposed in said distal section pivotable about a pivot axis generally transverse to said longitudinal axis;

a means for rotating said reflector relative to said distal section; and an objective optical system disposed in said distal section;

wherein said main shaft is flexible;

wherein said means for rotating said distal section comprises a flexible first internal shaft running down the interior of said main shaft;

wherein said means for rotating said reflector comprises a second internal shaft within said first internal shaft; and wherein said second internal shaft houses a fiber optic bundle.

20. A variable direction of view endoscope with a modular distal section comprising:

a main shaft;

a rigid distal section connected to said main shaft having a longitudinal axis, wherein said rigid distal section is rotatable relative to said main shaft;

a means for rotating said distal section relative to said main shaft;

a slip-ring for providing electrical power across the rotary interface between said main shaft and said distal section;

a reflector disposed in said distal section pivotable about a pivot axis generally transverse to said longitudinal axis;

a means for rotating said reflector relative to said distal section; and an objective optical system disposed in said distal section.

* * * * *